| (12) | United States Patent | (10) Patent No.: | US 10,918,417 B2 |
|---|---|---|---|
| | Lin et al. | (45) Date of Patent: | Feb. 16, 2021 |

(54) PEDICLE SCREW SYSTEM WITH SINGLE PLANE MOTION AND AXIAL ROTATION

(71) Applicants: National Yang-Ming University, Taipei (TW); Chang Gung Memorial Hospital, Linkou, Taoyuan (TW)

(72) Inventors: Chun-Li Lin, Taipei (TW); Po-Liang Lai, Taoyuan (TW); Po-Yi Liu, Taipei (TW)

(73) Assignees: NATIONAL YANG-MING UNIVERSITY, Taipei (TW); CHANG GUNG MEMORIAL HOSPITAL, Taoyuan (TW)

( * ) Notice: Subject to any disclaimer, the term of this patent is extended or adjusted under 35 U.S.C. 154(b) by 114 days.

(21) Appl. No.: 15/700,739

(22) Filed: Sep. 11, 2017

(65) Prior Publication Data

US 2018/0263662 A1    Sep. 20, 2018

(30) Foreign Application Priority Data

Mar. 17, 2017  (TW) .................................. 106108972

(51) Int. Cl.
    *A61B 17/70*    (2006.01)
    *A61B 17/86*    (2006.01)
    *A61B 17/58*    (2006.01)

(52) U.S. Cl.
    CPC ...... *A61B 17/7032* (2013.01); *A61B 17/7038* (2013.01); *A61B 17/8605* (2013.01); *A61B 17/8685* (2013.01); *A61B 17/7002* (2013.01); *A61B 17/862* (2013.01); *A61B 17/863* (2013.01)

(58) Field of Classification Search
CPC .. A61B 17/7032; A61B 17/7034–7035; A61B 17/7002; A61B 17/7005; A61B 17/704; A61B 17/7046; A61B 17/7037–7038; A61B 17/861–862; A61B 17/8605; A61B 17/8615; A61B 17/8685
USPC ..................................... 606/70–71, 246–299
See application file for complete search history.

(56) References Cited

U.S. PATENT DOCUMENTS

| 5,910,142 | A | * | 6/1999 | Tatar | .................... | A61B 17/704 |
|---|---|---|---|---|---|---|
| | | | | | | 606/272 |
| 2002/0022842 | A1 | * | 2/2002 | Horvath | ............. | A61B 17/7032 |
| | | | | | | 606/302 |
| 2003/0055426 | A1 | * | 3/2003 | Carbone | ............ | A61B 17/7034 |
| | | | | | | 606/271 |
| 2005/0177154 | A1 | * | 8/2005 | Moumene | .......... | A61B 17/7032 |
| | | | | | | 606/276 |

(Continued)

*Primary Examiner* — Jessica Weiss
(74) *Attorney, Agent, or Firm* — Muncy, Geissler, Olds and Lowe, P.C.

(57) ABSTRACT

The present invention provides a pedicle screw, which includes a screw head, a screw body, a screw rod and a screw cap. The screw body includes a ball-liked arc-shaped buckle portion and a column-liked thread portion. The screw head includes a semi-sphere part with an arc-shaped dimple on one end and a U-shaped cavity on the other end. The U-shaped cavity connects with the arc-shaped dimple. Furthermore, the Arc-shaped dimple connects with the arc-shaped buckle portion. The Arc-shaped dimple includes an opening on its top to allow the screw body passing through. The U-shaped cavity includes an opening, which includes a female thread to fix the screw rod in the U-shaped cavity by a male thread on the screw cap.

5 Claims, 12 Drawing Sheets

(56) References Cited

U.S. PATENT DOCUMENTS

2006/0200128 A1* 9/2006 Mueller ............. A61B 17/7032
  606/308
2015/0190176 A1* 7/2015 Jackson ............... A61B 17/704
  606/272

* cited by examiner

PEDICLE SCREW SYSTEM WITH SINGLE PLANE MOTION AND AXIAL ROTATION

CROSS-REFERENCE TO RELATED APPLICATIONS

This application claims priority to Taiwan Application Serial Number 106108972, filed Mar. 17, 2017, which is herein incorporated by reference.

FIELD OF THE INVENTION

The present disclosure relates to a bone screw assembly. More particularly, the present disclosure relates to a pedicle screw.

BACKGROUND OF THE INVENTION

The human spine consists of 33 to 34 vertebras and an intervertebral disc for buffering. In general, the vertebras are arranged in a straight line when viewed in a coronal plane and in a S-shaped curve when viewed in a sagittal plane. In view of a horizontal plane, the vertebral body faces forward, and the spinous process faces backward. When an abnormal bending occurred, the spine can be bent in a C-shape (that is, a simple curve or an entire curve) or S-shape (that is, a composite curve).

Scoliosis not only existed in the coronal plane but also in the sagittal plane and the horizontal plane. When a Cobb angle is larger than 40 degrees, complications will occur. Thus, a surgical treatment will be advanced.

In clinical, a pedicle screw is most often utilized for correcting scoliosis. According to the structure, the pedicle screw can be divided into two categories, that is, a monoaxial pedicle screw and a polyaxial pedicle screw. The polyaxial pedicle screw performs a polyaxial action through its thread head so that the polyaxial screw can be assembled with a rod easily during the surgical treatment. Even the occurrence of the stress concentration can be efficiently reduced. However, a good treatment effect can be achieved in the sagittal plane and the coronal plane but cannot be achieved in the axial plane.

On the contrary, the monoaxial pedicle screw has a better treatment effect, and a vertebral body derotation can be achieved in the axial plane through the monoaxial pedicle screw. However, it is hard to assemble the monoaxial pedicle screw with the rod so as to result in a vertebral fracture and an additional stress concentration.

In addition, when treating scoliosis or other spine degenerative diseases with pedicle screw system, complications, such as loose of the screws, removing of the screws, and loss of reduction, occurred.

Accordingly, how to solve the difficulty and inconvenience of using the current pedicle screw is urgent. Thus, the present disclosure provides a pedicle screw for solving the abovementioned problems.

SUMMARY OF THE INVENTION

The present disclosure provides a pedicle screw. An angle of a screw head of the pedicle screw can be adjusted to allow a screw rod to insert therein. A notch of the engagement between the screw head and the screw rod always faces upward and downward regardless of a depth of inserting a screw body of the pedicle screw. Thus, the screw body can be limited in the axial plane, and it is favorable to perform the vertebral body derotation.

Accordingly, the present disclosure provides a pedicle screw. The pedicle screw includes a screw head and a screw body. The screw head includes a U-shaped cavity, in which the U-shaped cavity is formed on an inner wall of the screw head and comprises a first groove and a second groove. The first groove is formed on an upper portion of the U-shaped cavity, and the second groove is formed on a lower portion of the U-shaped cavity and communicated with the first groove. In addition, an arc-shaped dimple is disposed between the first groove and the second groove. The screw body includes an arc-shaped buckle portion a d a thread portion. The arc-shaped buckle portion is disposed on one end of the screw body, and the thread portion is disposed on the other end of the screw body. The thread portion can pass through the U-shaped cavity and the second groove from the first groove, and the arc-shaped buckle portion can fall into and be against to the arc-shaped dimple. In addition, the thread portion passes through the second groove to be entirely exposed, and the arc-shaped buckle portion is rotatable in the arc-shaped dimple to allow the screw body to perform a simple pendulum (e.g., swing) and a self-rotation in the second groove.

BRIEF DESCRIPTION OF THE DRAWINGS

The disclosure can be more fully understood by reading the following detailed description of the embodiment, with reference made to the accompanying drawings as follows.

DETAILED DESCRIPTION OF THE INVENTION

The present disclosure relates to biotechnology medical materials, and the biotechnology medical materials is applied in spine-related treatments for assisting spinal fusion. In particular, the present disclosure can be applied on treatments for temporary and long-term instability or deformity of neck, thoracic, lumbar, and psoriasis, vertebral degeneration and obvious nerve damage, fracture, displacement, scoliosis, kyphosis, spinal tumors, and the previous integration of pseudarthrosis.

Figure 1:
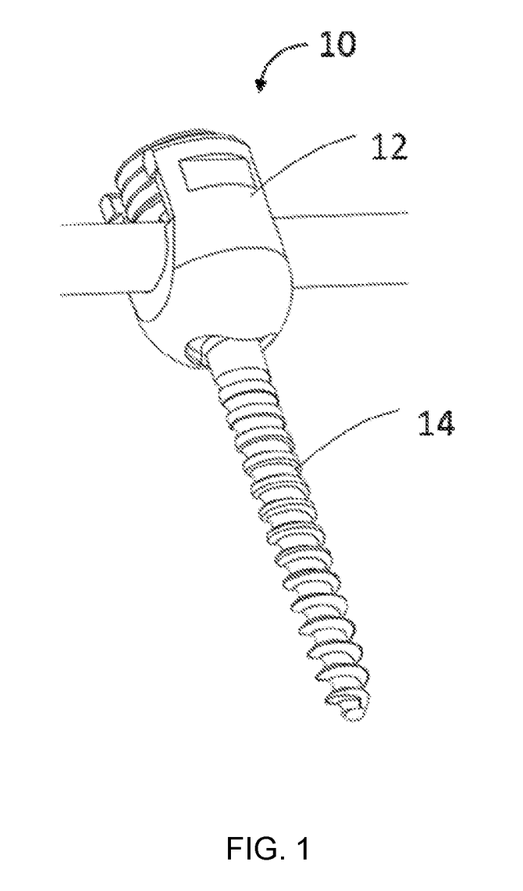
FIG. 1 is a schematic view of a pedicle screw according to an embodiment of the present disclosure.
Figure 2A:
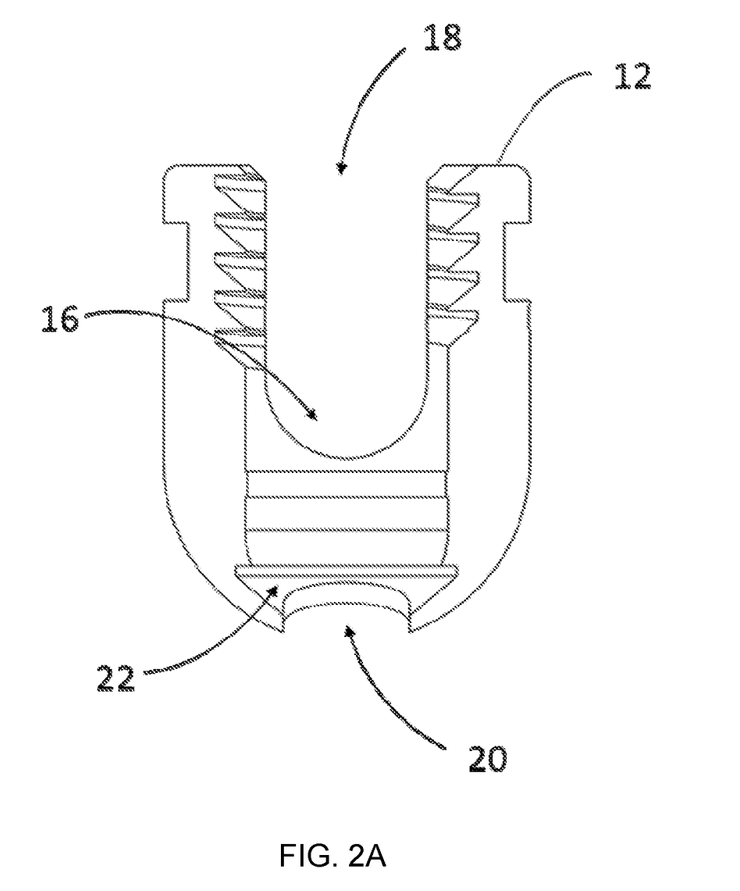
FIG. 2A is a schematic view of a screw head according to the embodiment of the present disclosure.
Figure 2B:
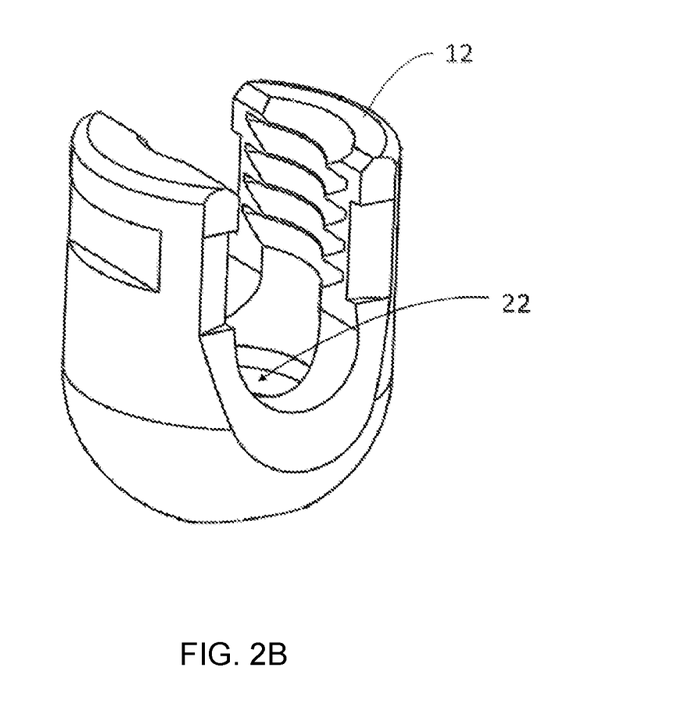
FIG. 2B is another schematic view of a screw head according to the embodiment of the present disclosure.
Figure 3:
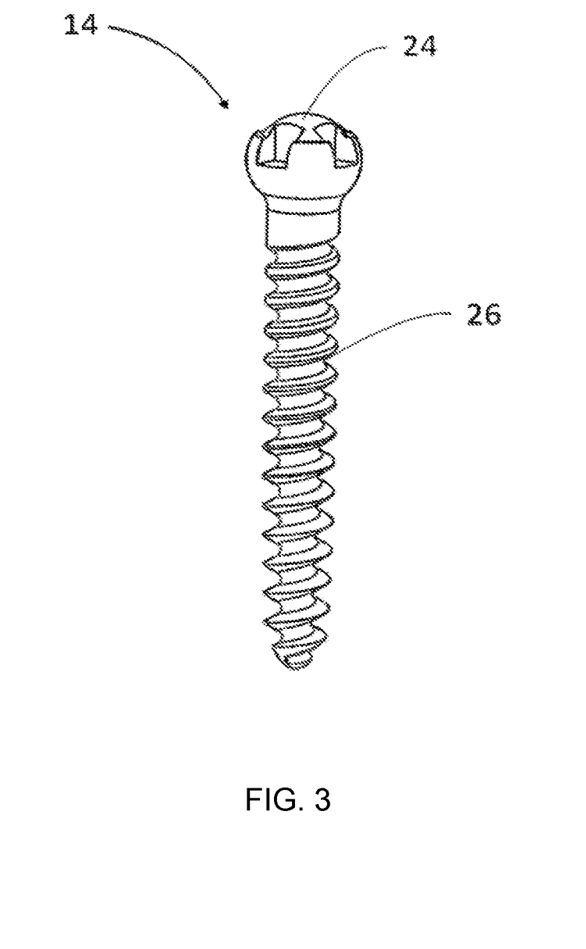
FIG. 3 is a schematic view of a screw body according to an embodiment of the present disclosure.
Figure 4A:
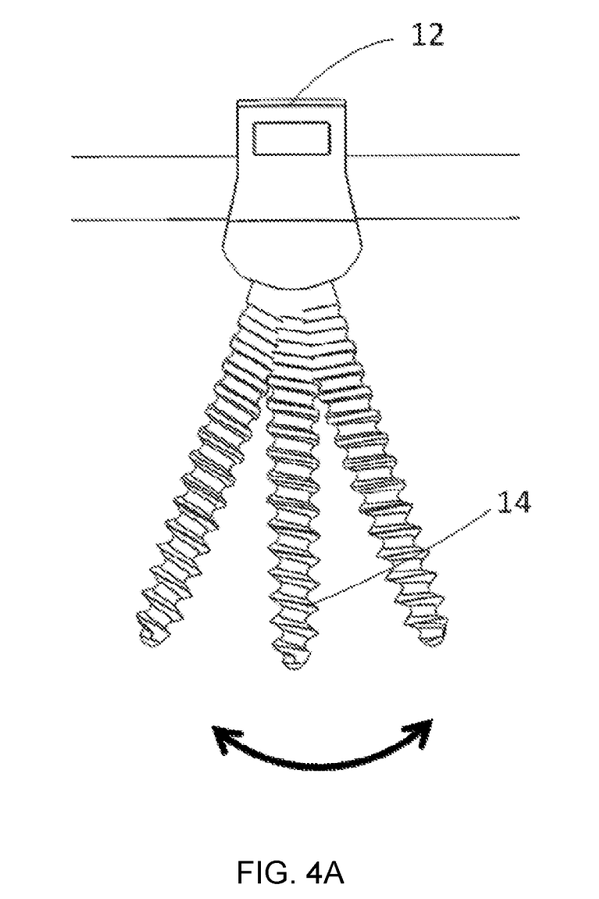
FIG. 4A is a schematic view showing a simple pendulum of a pedicle screw according to an embodiment of the present disclosure.
Figure 4B:
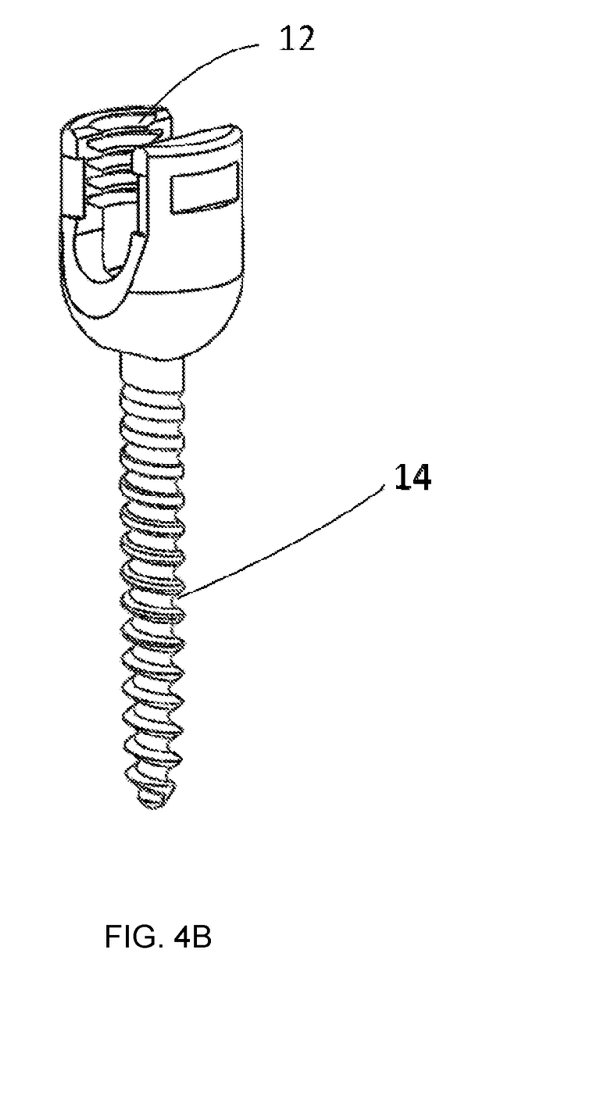
FIG. 4B is a schematic view showing a self-rotation of a pedicle screw according to an embodiment of the present disclosure.

Please refer to FIG. 1, FIG. 2A, FIG. 2B, FIG. 3, FIG. 4A and FIG. 4B. FIG. 1 is a schematic view of a pedicle screw according to an embodiment of the present disclosure, FIG. 2A is a schematic view of a screw head according to the embodiment of the present disclosure, FIG. 2B is another schematic view of a screw head according to the embodiment of the present disclosure, FIG. 3 is a schematic view of a screw body according to an embodiment of the present disclosure, FIG. 4A is a schematic view showing a simple pendulum of a pedicle screw according to an embodiment of the present disclosure, and FIG. 4B is a schematic view showing a self-rotation of a pedicle screw according to an embodiment of the present disclosure.

In FIG. 1, the pedicle screw 10 of the present disclosure includes a screw head 12 and a screw body 14. As shown in FIG. 2A and FIG. 2B, a U-shaped cavity 16 is formed on an inner wall of the screw head 12. A first groove 18 is formed on an upper portion of the U-shaped cavity 16, and a second groove 20 is formed on a lower portion of the U-shaped cavity 16 and communicated with the first groove 20. An arc-shaped dimple 22 is disposed between the first groove 18 and the second groove 20.

Then, an arc-shaped buckle portion 24 is disposed on one end of the screw body 14, and a thread portion 26 is disposed on the other end of the screw body 14. The thread portion 26 passes through the U-shaped cavity 16 and the second groove 20 from the first groove 18 to be entirely exposed out of the second groove 20. The arc-shaped buckle portion 24 is rotatable in the arc-shaped dimple 22 to allow the screw body 14 to perform a simple pendulum and a self-rotation in the second groove 20 so as to allow the arc-shaped buckle portion 24 to fall into and be against to the arc-shaped dimple 22.

Figure 5:
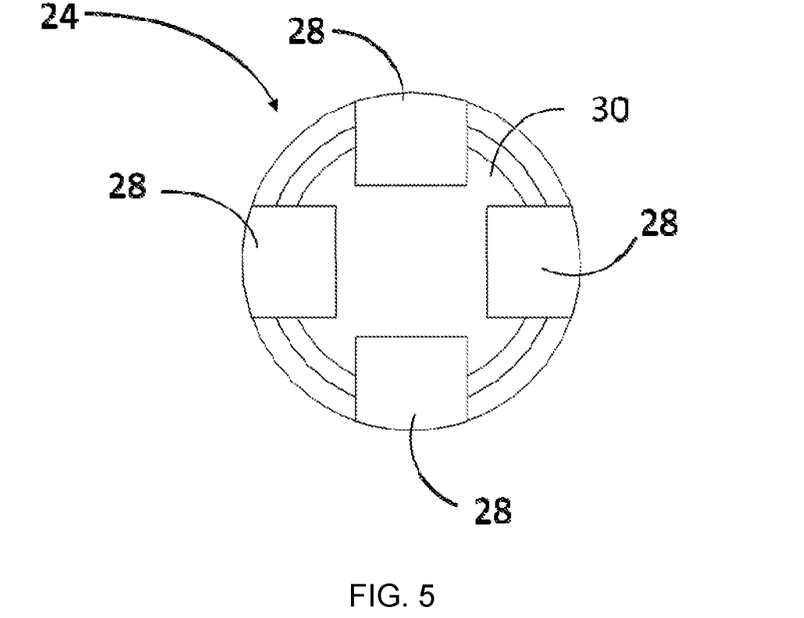
FIG. 5 is another schematic view of a screw body according to an embodiment of the present disclosure.

Please refer to FIG. 5 in conjunction with FIG. 1, FIG. 3 and FIG. 4B. FIG. 5 is another schematic view of a screw body according to an embodiment of the present disclosure. As shown in the figures, the screw body 14 further includes at least one polygonal groove 28. The polygonal groove 28 is disposed on a top part 30 of the arc-shaped buckle portion 24 and can rotate the arc-shaped buckle portion 24 by an external force to allow the screw body 14 to perform the self-rotation. When the screw body 14 includes two polygonal grooves 28, each of the polygonal grooves 28 is symmetrically disposed on two sides of the top part 30 of the arc-shaped buckle portion 24. When the screw body 14 includes four polygonal grooves 28, each of the polygonal grooves 28 is cross-symmetrically disposed on four sides of the top part 30 of the arc-shaped buckle portion 24.

It is noted that FIG. 5 is only a schematic view for clearly illustrating the present disclosure, and the two polygonal grooves 28 or the four polygonal grooves 28 are provided as examples. However, the quantity of the polygonal groove 28 can be increased or decreased depending on the actual needs.

Figure 6A:
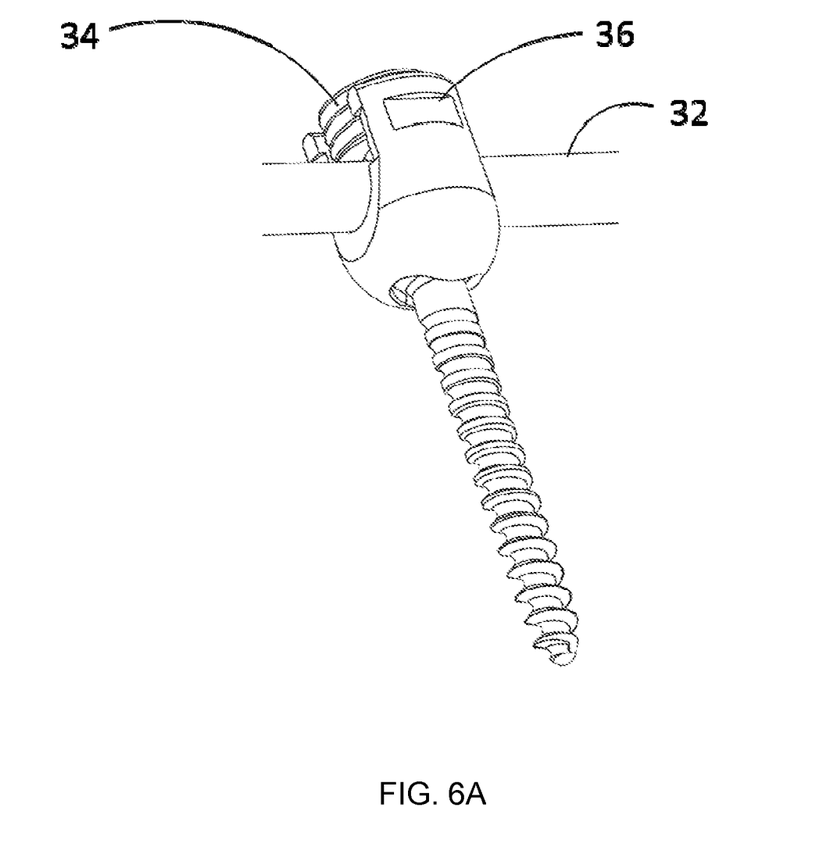
FIG. 6A is a schematic view of a pedicle screw having a screw rod according to an embodiment of the present disclosure.
Figure 6B:
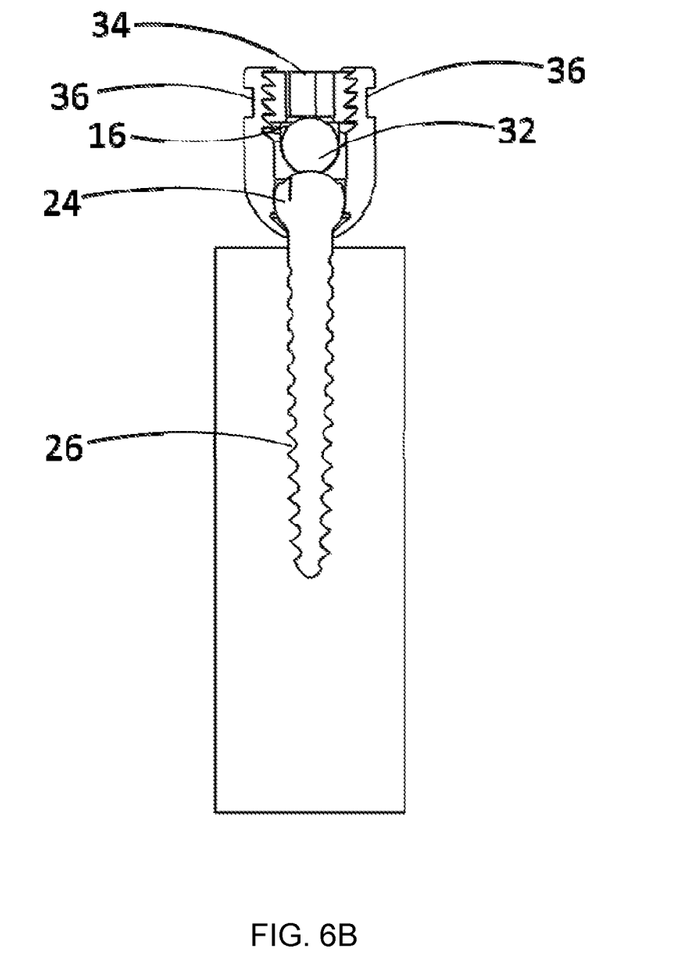
FIG. 6B is another schematic view of a pedicle screw having a screw rod according to an embodiment of the present disclosure.

FIG. 6A is a schematic view of a pedicle screw having a screw rod according to an embodiment of the present disclosure, and FIG. 6B is another schematic view of a pedicle screw having a screw rod according to an embodiment of the present disclosure. In addition, FIG. 1 is referred at the same time. In the figures, the pedicle screw 10 further includes a screw rod 32 and a screw cap 34. The screw rod 32 is disposed in the U-shaped cavity 16 and located above the arc-shaped buckle portion 24. The screw cap 34 enters from the first groove 18 and disposed above the screw rod 32 for locking the first groove 18.

In addition, different types of the opening of the screw head 12 of the pedicle screw 10 will allow the screw body 14 only to act in a specific plane and self-rotate along the long axis. Thus, an activity of a plane to be corrected will be limited to allow the pedicle screw 10 to rotate the vertebral body easily by controlling the screw head. The screw body 14 can rotate axially for adjusting the depth of inserting the screw body. The U-shaped cavity 16 of the screw head 12 can face upward to connect with the screw rod 32 regardless of the depth of inserting the screw body 14. Because the activity of the specific plane is maintained, a specific angle between the screw rod 32 and the U-shaped cavity 16 of the screw head 12 can be avoided for eliminating unstable situations.

In the pedicle screw 10, the first groove 18 is a ditch groove, the second groove 20 is a slit groove, the screw body 14 is a long column-like shaft, the screw rod 32 is a long column-like connecting bar, the screw rod 32 extends outwards from two sides of the first groove 18, and the slit of the second groove 20 is larger than a cross-sectional area of the screw body 14. Moreover, a volume of a lower portion of the screw rod 32 is equal to a volume of the lower portion of the U-shaped cavity 16, and a volume of the screw cap 34 is equal to a volume of the first groove 18. An outer surface of the screw cap 34 has a male thread, an inner surface of the first groove 18 has a female thread, and the male thread of the screw cap 34 is able to screw in or screw out the female thread of the first groove 18. In particular, the male thread and the female thread are jagged threads. In addition, the screw head 12 further includes two plane grooves 36 disposed on an outer surface of the screw head 12. A direction of inserting the screw rod 32 is parallel vertical to a long diameter of the second groove 20.

Figure 7A:
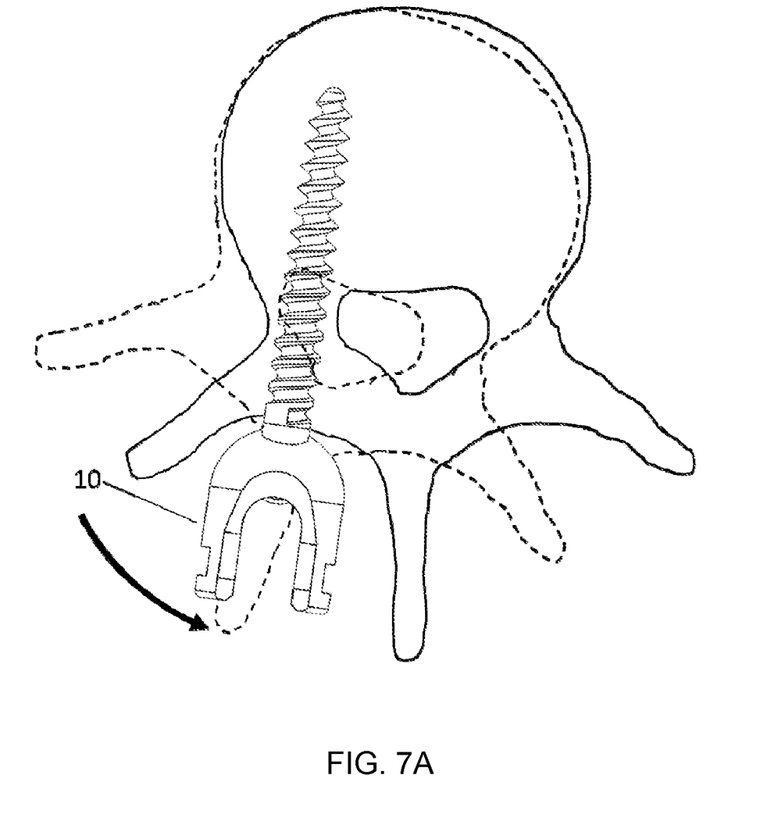
FIG. 7A is a schematic view showing a rotation of a vertebral body driven by a screw head according to an embodiment of the present disclosure.
Figure 7B:
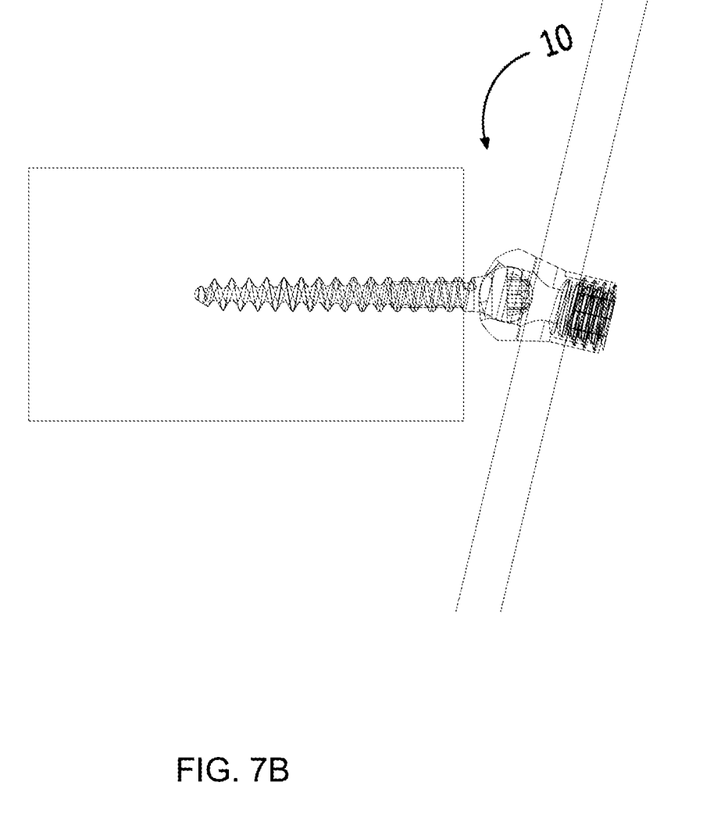
FIG. 7B is a schematic view showing a simple pendulum of a screw body according to an embodiment of the present disclosure.

Please refer to FIG. 7A and FIG. 7B, which are schematic views for illustrating a simple pendulum and a self-rotation of the screw body in the present disclosure. In the meanwhile, referring back to FIG. 4A and FIG. 4B, the screw body 14 of the pedicle screw 10 can perform a simple pendulum and a self-rotation. Thus, the screw body 14, which is in the second groove 20, is able to bend outwards to 30 degrees or leftwards and rightwards to 60 degrees.

Figure 8:
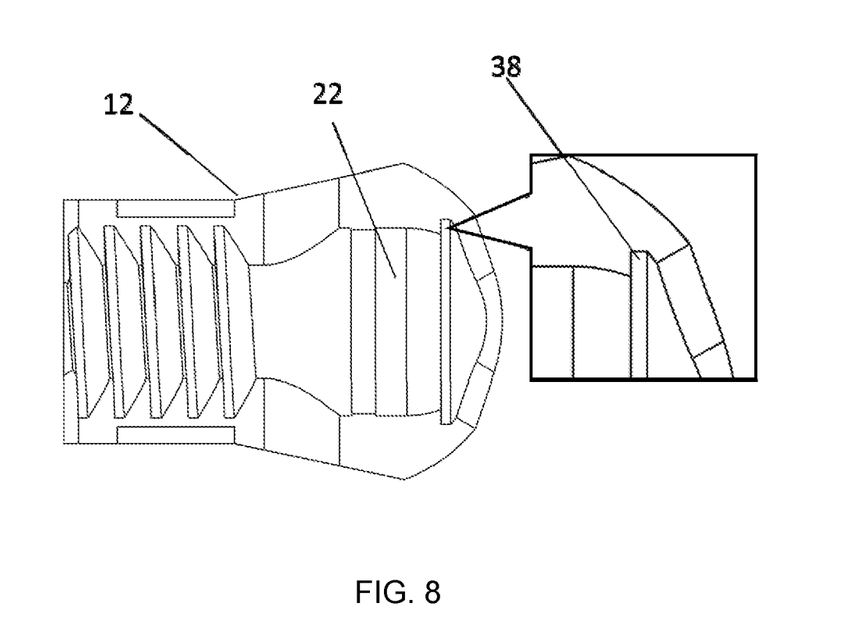
FIG. 8 is a schematic view of a screw head having an engaging groove according to an embodiment of the present disclosure.

FIG. 8 is a schematic view of a screw head having an engaging groove according to an embodiment of the present disclosure. As shown in the figure, the screw head 12 of the present disclosure further includes an engaging groove 38 disposed on a bottom surface of the arc-shaped dimple 22 for fixing the arc-shaped buckle portion 24.

Accordingly, the present invention provides a pedicle screw 10. The pedicle screw 10 includes a screw head 12, a screw body 14, a screw rod 32 and a screw cap 34. The screw head 12 includes a ball-liked arc-shaped buckle portion 24 and a column-liked thread portion 26. The screw head 12 includes a semi-sphere part with an arc-shaped dimple 22 on one end and a U-shaped cavity 16 on the other end. The U-shaped cavity 16 connects with the arc-shaped dimple 11. Furthermore, the Arc-shaped dimple 24 connects with the arc-shaped buckle portion 22. The Arc-shaped dimple 22 includes an opening on its top to allow the screw body 14 passing through. The U-shaped cavity 16 includes an opening, which includes a female thread to fix the screw rod 32 in the U-shaped cavity 16 by a male thread on the screw cap 34.

To sum up, the effects can be achieved by the pedicle screw of the present disclosure are listed as follows: (1) the angle of the screw head can be adjusted for inserting the screw rod; (2) The notch of the engagement between the screw head and the screw rod always faces upward and downward regardless of a depth of inserting a screw body of the pedicle screw; (3) The screw body can be limited in the axial plane, and it is favorable to perform the vertebral body derotation; and (4) The ditch groove and the slit groove are parallel and vertical to each other so as to be applied to different treatment. The pedicle screw of the present disclosure can be set up by only four parts, that is, the screw head, the screw body, the screw rod and the screw cap so as to reduce the manufacturing cost. Although the screw head used in the commercial pedicle screw has a round opening for increasing the activity of the screw body, the correction of the vertebral body is difficult. The second groove of the screw head according to the present disclosure is a slit groove to limit the activity of partial planes so as to achieve the correction effect and maintain the activity of the specific plane. Thus, the screw rod is easier to be assembled.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A pedicle screw assembly, comprising:
 a screw head including a U-shaped cavity and having a longitudinal axis therethrough, wherein the U-shaped cavity is formed through an inner wall of the screw head and comprises:
  a first opening formed through an upper portion of the U-shaped cavity;
  a second opening, coaxial with the first opening, formed through a lower portion of the U-shaped cavity and in communication with the first opening, the second opening being slit-shaped;
  an arc-shaped dimple disposed between the first opening and the second opening; and
  an engaging groove disposed on a bottom surface of the arc-shaped dimple;
 a screw body having an elongate column-shaped shaft and comprising:
  an arc-shaped head disposed on a first end of the screw body;
  four polygonal grooves disposed on a top part of the arc-shaped head, each of the four polygonal grooves being disposed on a respective side of four sides of a top part of the arc-shaped head such that the four polygonal grooves are arranged symmetrically about the top part of the arc-shaped head, wherein the four polygonal grooves are configured to facilitate rotation of the arc-shaped head upon application of an external force to allow the screw body to rotate; and
  a thread portion disposed on a second end of the screw body, a thread of the thread portion configured to pass through the U-shaped cavity such that the thread portion is entirely exposed from the second opening,
 a screw rod disposed in the U-shaped cavity and located above the arc-shaped head; and
 a screw cap configured to be inserted into the first opening and disposed above the screw rod,
 wherein a direction of inserting the screw rod is parallel to a diameter of the second opening,
 wherein the engaging groove is configured to fix the arc-shaped head, and
 wherein the arc-shaped head is rotatable in the arc-shaped dimple to allow the screw body to swing and rotate in the second opening and allow the arc-shaped head to fall into and contact the arc-shaped dimple,
 wherein the screw body is able to swing offset from the longitudinal axis of the screw head by 30 degrees through the second opening,
 wherein the screw body swings and rotates restrictively in a single specific plane through the second opening to provide the pedicle screw assembly to perform a vertebral body de-rotation.

2. The pedicle screw assembly of claim 1, wherein an outer surface of the screw cap has a male thread, an inner surface of the first opening has a female thread, and
 wherein the male thread of the screw cap is configured to screw in or screw out of the female thread of the inner surface of the first opening.

3. The pedicle screw assembly of claim 2, wherein the male thread and the female thread are jagged threads.

4. The pedicle screw assembly of claim 1, wherein the screw head further comprises:
 two planar grooves disposed on an outer surface of the screw head.

5. A pedicle screw assembly, comprising:
 a screw head including a U-shaped cavity and having a longitudinal axis therethrough, wherein the U-shaped cavity is formed through an inner wall of the screw head and comprises:
  a first opening formed through an upper portion of the U-shaped cavity;
  a second opening, coaxial with the first opening, formed through a lower portion of the U-shaped cavity and in communication with the first opening, the second opening being slit-shaped;
  an arc-shaped dimple disposed between the first opening and the second opening; and
  an engaging groove disposed on a bottom surface of the arc-shaped dimple;
 a screw body having an elongate column-shaped shaft and comprising:
  an arc-shaped head disposed on a first end of the screw body;
  four polygonal grooves disposed on a top part of the arc-shaped head, each of the four polygonal grooves being disposed on a respective side of four sides of the top part of the arc-shaped head such that the four polygonal grooves are arranged symmetrically about the top part of the arc-shaped head, wherein the four polygonal grooves are configured to facilitate rotation of the arc-shaped head upon application of an external force to allow the screw body to rotate; and
  a thread portion disposed on a second end of the screw body, a thread of the thread portion configured to pass through the U-shaped cavity such that the thread portion is entirely exposed from the second opening;
 a screw rod disposed in the U-shaped cavity and located above the arc-shaped head; and
 a screw cap configured to be inserted into the first opening and disposed above the screw rod,
 wherein a direction of inserting the screw rod is vertical to a diameter of the second opening,
 wherein the engaging groove is configured to fix the arc-shaped head, wherein the arc-shaped head is rotatable in the arc-shaped dimple to allow the screw body to swing and rotate in the second opening and allow the arc-shaped head to fall into and contact the arc-shaped dimple, wherein the screw body is able to swing offset from the longitudinal axis of the screw head by 30 degrees through the second opening, and wherein the screw body swings and rotates restrictively in a single specific plane through the second opening.

* * * * *